(12) United States Patent
Smith et al.

(10) Patent No.: US 10,614,949 B2
(45) Date of Patent: Apr. 7, 2020

(54) ELECTROSTATIC SHIELDING OF PLANAR MAGNETIC DEVICES OF ELECTROSURGICAL GENERATORS

(71) Applicant: COVIDIEN LP, Mansfield, MA (US)

(72) Inventors: Robert B. Smith, Loveland, CO (US); Daniel A. Friedrichs, Aurora, CO (US); Steven C. Rupp, Arvada, CO (US)

(73) Assignee: Covidien LP, Mansfield, MA (US)

( * ) Notice: Subject to any disclaimer, the term of this patent is extended or adjusted under 35 U.S.C. 154(b) by 748 days.

(21) Appl. No.: 15/182,815

(22) Filed: Jun. 15, 2016

(65) Prior Publication Data

US 2017/0365398 A1  Dec. 21, 2017

(51) Int. Cl.
*A61B 18/00* (2006.01)
*H01F 27/28* (2006.01)
*H01F 27/36* (2006.01)
*A61B 18/12* (2006.01)

(52) U.S. Cl.
CPC ........ *H01F 27/2885* (2013.01); *A61B 18/12* (2013.01); *A61B 18/1206* (2013.01); *H01F 27/2804* (2013.01); *H01F 27/365* (2013.01); *A61B 2018/00827* (2013.01); *A61B 2018/1266* (2013.01); *H01F 2027/2809* (2013.01)

(58) Field of Classification Search
CPC ........ H01F 2027/2809; H01F 27/2804; H01F 27/2885; H01F 27/365; H01F 27/288; H01F 27/36; A61B 18/12; A61B 18/1206; A61B 2018/00827; A61B 2018/1266; H01Q 15/14; H05K 2201/0707; H05K 2201/0715; H05K 2201/09; H05K 2201/09218; H01L 2924/3025

See application file for complete search history.

(56) References Cited

U.S. PATENT DOCUMENTS

| | | |
|---|---|---|
| 5,360,941 A | 11/1994 | Roes |
| 8,629,746 B2 | 1/2014 | Lu |
| 9,366,703 B2 | 6/2016 | Gilbert |
| 2002/0096736 A1 | 7/2002 | Brennan et al. |
| 2007/0052062 A1* | 3/2007 | Ding ............ H01L 23/5223 257/528 |
| 2011/0028963 A1 | 2/2011 | Gilbert |
| 2011/0054460 A1 | 3/2011 | Gilbert |
| 2011/0115562 A1 | 5/2011 | Gilbert |

(Continued)

FOREIGN PATENT DOCUMENTS

| | | |
|---|---|---|
| CN | 105185778 A | 12/2015 |
| EP | 3028659 A2 | 6/2016 |

OTHER PUBLICATIONS

European Search Report dated Dec. 13, 2017 issued in corresponding EP Appln. No. 17175957.

*Primary Examiner* — Eun Hwa Kim
*Assistant Examiner* — Rachel A. Vierra
(74) *Attorney, Agent, or Firm* — Carter, DeLuca & Farrell LLP

(57) ABSTRACT

An electronic device includes: a multilayered dielectric substrate including a plurality of dielectric layers; a planar magnetic device disposed on at least one internal dielectric layer of the plurality of dielectric layers; and an overlapping shield assembly including a first shield layer and a second shield layer separated by at least one of the plurality of dielectric layers.

8 Claims, 6 Drawing Sheets

(56) References Cited

U.S. PATENT DOCUMENTS

| | | |
|---|---|---|
| 2013/0207767 A1 | 8/2013 | Worthington |
| 2014/0167733 A1* | 6/2014 | Buck .................. H01F 5/003 324/76.11 |
| 2015/0025523 A1 | 1/2015 | Friedrichs et al. |
| 2015/0088117 A1 | 3/2015 | Gilbert et al. |
| 2016/0151109 A1 | 6/2016 | Buck et al. |

* cited by examiner

ELECTROSTATIC SHIELDING OF PLANAR MAGNETIC DEVICES OF ELECTROSURGICAL GENERATORS

BACKGROUND

Technical Field

The present disclosure relates to shielding of planar magnetic devices, such as those used in an electrosurgical generator. In particular, the present disclosure relates to shielding members disposed on a printed circuit board containing the planar magnetic devices, such as current sense coils and transformers. The shielding members according to the present disclosure are configured to shield planar magnetics from stray electromagnetic fields.

Background of Related Art

Electrosurgery involves application of high radio frequency ("RF") electrical current to a surgical site to cut, ablate, desiccate, or coagulate tissue. In monopolar electrosurgery, a source or active electrode delivers RF alternating current from the electrosurgical generator to the targeted tissue. A patient return electrode is placed remotely from the active electrode to conduct the current back to the generator.

In bipolar electrosurgery, return and active electrodes are placed in close proximity to each other such that an electrical circuit is formed between the two electrodes (e.g., in the case of an electrosurgical forceps). In this manner, the applied electrical current is limited to the body tissue positioned between the electrodes. Accordingly, bipolar electrosurgery generally involves the use of instruments where it is desired to achieve a focused delivery of electrosurgical energy between two electrodes.

Electrosurgical generators may include planar magnetic devices, (e.g., transformers and/or inductors), which are constructed using multilayered printed circuit boards. Planar magnetic devices are commonly used to increase magnetic coupling between conducting layers while decreasing skin effect by taking advantage of the proximity and large surface areas of the parallel planes. However, this also increases voltage coupling. This can result in decreased high frequency performance of the planar components, such as increased crosstalk and susceptibility to external electromagnetic interference ("EMI") from the electrosurgical generator. Conventional, e.g., non-planar, magnetic devices usually include EMI shields, such as solid or mesh copper shields, which are not suitable in planar magnetic devices. Although adding a solid or mesh electrostatic shield to a planar magnetic device would shield the device, it would also render the device non-functional. In conventional magnetic devices, a solid shield can be added incorporated into the device because the three dimensional shape of the magnetic device allows the shield to be placed orthogonally to the magnetic field, thereby avoiding any interaction between the field and the shield. However, a planar magnetic device, which is effectively a two dimensional structure, construction techniques limit placement of the solid shields in the desired location, with respect to blocking EMI.

Furthermore, any such shielding conductors disposed near the winding of the planar component would diminish the magnetic field of the signal, which would generate strong currents, effectively shorting the windings of the planar component. Thus, there remains a need to shield planar magnetics from stray electromagnetic fields.

SUMMARY

According to one embodiment of the present disclosure, an electronic device includes: a multilayered dielectric substrate including a plurality of dielectric layers; a planar magnetic device disposed on at least one internal dielectric layer of the plurality of the dielectric layers; and an overlapping shield assembly including a first shield layer and a second shield layer separated by at least one of the plurality of dielectric layers.

According to one aspect of the above embodiment, the planar magnetic device is a sense transformer. The sense transformer includes: a first outer coil configured to detect a first magnetic field generated by a current; a second outer coil configured to detect the first magnetic field, the second outer coil further configured to cancel an electrical field induced in the first outer coil; and an inner conductor disposed between the first outer coil and the second outer coil, the inner conductor configured to detect a second magnetic field generated by the current. Each of the first outer coil, the second outer coil, and the inner conductor is disposed on a corresponding internal dielectric layer of the plurality of dielectric layers.

According to another embodiment of the present disclosure, an electrosurgical generator is disclosed. The electrosurgical generator includes: a power supply configured to output a direct current; a power converter coupled to the power supply, the power converter configured to convert the direct current into a radio frequency current; at least one lead coupling the power converter to a terminal configured to couple to an electrosurgical instrument; and a current sensor configured to sense the radio frequency current. The current sensor includes: a multilayered dielectric substrate including a plurality of dielectric layers; at least one component of the current sensor disposed on at least one internal dielectric layer of the plurality of the dielectric layers; and an overlapping shield assembly including a first shield layer and a second shield layer separated by at least one of the plurality of dielectric layers.

According to one aspect of any of the above embodiments, the first shield layer includes a plurality of first strips and the second shield layer includes a plurality of second strips. Each of the plurality of first strips has a first width and the plurality of first strips are separated by a first gap width. Each of the plurality of second strips has a second width and the plurality of second strips are separated by a second gap width. The first width is substantially equal to the second gap width and the second width is substantially equal to the first gap width.

According to another aspect of any of the above embodiments, the first shield layer includes a first perimeter conductor coupled to each of the plurality of first strips and the second shield layer includes a second perimeter conductor coupled to each of the plurality of second strips. The first shield layer is electrically coupled to the second shield layer.

BRIEF DESCRIPTION OF THE DRAWINGS

The present disclosure may be understood by reference to the accompanying drawings, when considered in conjunction with the subsequent detailed description, in which.

DETAILED DESCRIPTION

Particular embodiments of the present disclosure will be described below with reference to the accompanying drawings. In the following description, well-known functions or constructions are not described in detail to avoid obscuring the present disclosure in unnecessary detail. Those skilled in the art will understand that embodiments of the present disclosure may be adapted for use with any electrosurgical system, generator, and/or instrument. It should also be appreciated that different electrical and mechanical connections and other considerations may apply to each particular type of instrument.

Briefly, an overlapping shield assembly according to the present disclosure is described below with respect to shielding planar magnetic devices in an electrosurgical generator. Although the present disclosure is described with respect to an electrosurgical generator, it is envisioned that the overlapping shield assembly may be utilized with any planar magnetic device in any electronic device in which EMI protection is desired.

The electrosurgical generator according to the present disclosure may be used in monopolar and/or bipolar electrosurgical procedures, including, for example, cutting, coagulation, ablation, and vessel sealing procedures. The generator may include a plurality of outputs for interfacing with various electrosurgical instruments (e.g., monopolar instruments, return electrode pads, bipolar electrosurgical forceps, footswitches, etc.). Further, the generator may include electronic circuitry configured to generate radio frequency energy specifically suited for powering electrosurgical devices operating in various electrosurgical modes (e.g., cut, blend, coagulate, division with hemostasis, fulgurate, spray, etc.) and procedures (e.g., monopolar, bipolar, vessel sealing).

Figure 1:
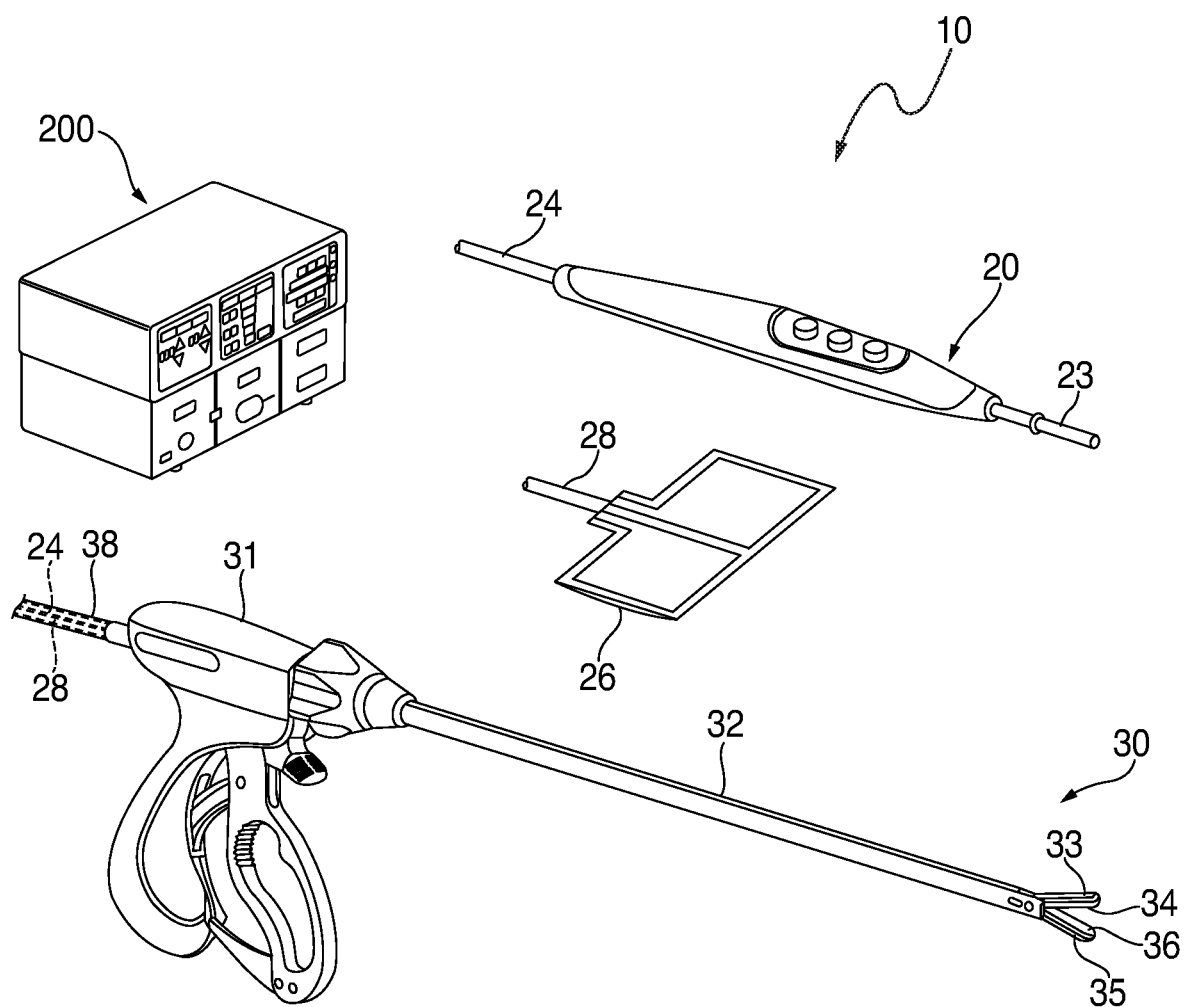
FIG. 1 is a perspective view of an electrosurgical system according to an embodiment of the present disclosure.

Referring to FIG. 1, an electrosurgical system 10 according to the present disclosure includes one or more monopolar electrosurgical instruments 20 having one or more active electrodes 23 (e.g., electrosurgical cutting probe, ablation electrode(s), etc.) for treating tissue of a patient. Electrosurgical alternating RF current is supplied to the instrument 20 by a generator 200 via a supply line 24 that is connected to an active terminal 350 (FIG. 3) of the generator 200, allowing the instrument 20 to cut, coagulate, and/or otherwise treat tissue. The RF current is returned to the generator 200 through a return electrode pad 26 via a return line 28 at a return terminal 352 (FIG. 3) of the generator 200. For monopolar operation, the system 10 may include a plurality of return electrode pads 26 that, in use, are disposed on a patient to minimize the chances of tissue damage by maximizing the overall contact area with the patient. In addition, the generator 200 and the return electrode pads 26 may be configured for monitoring tissue-to-patient contact to ensure that sufficient contact exists therebetween.

Figure 3:
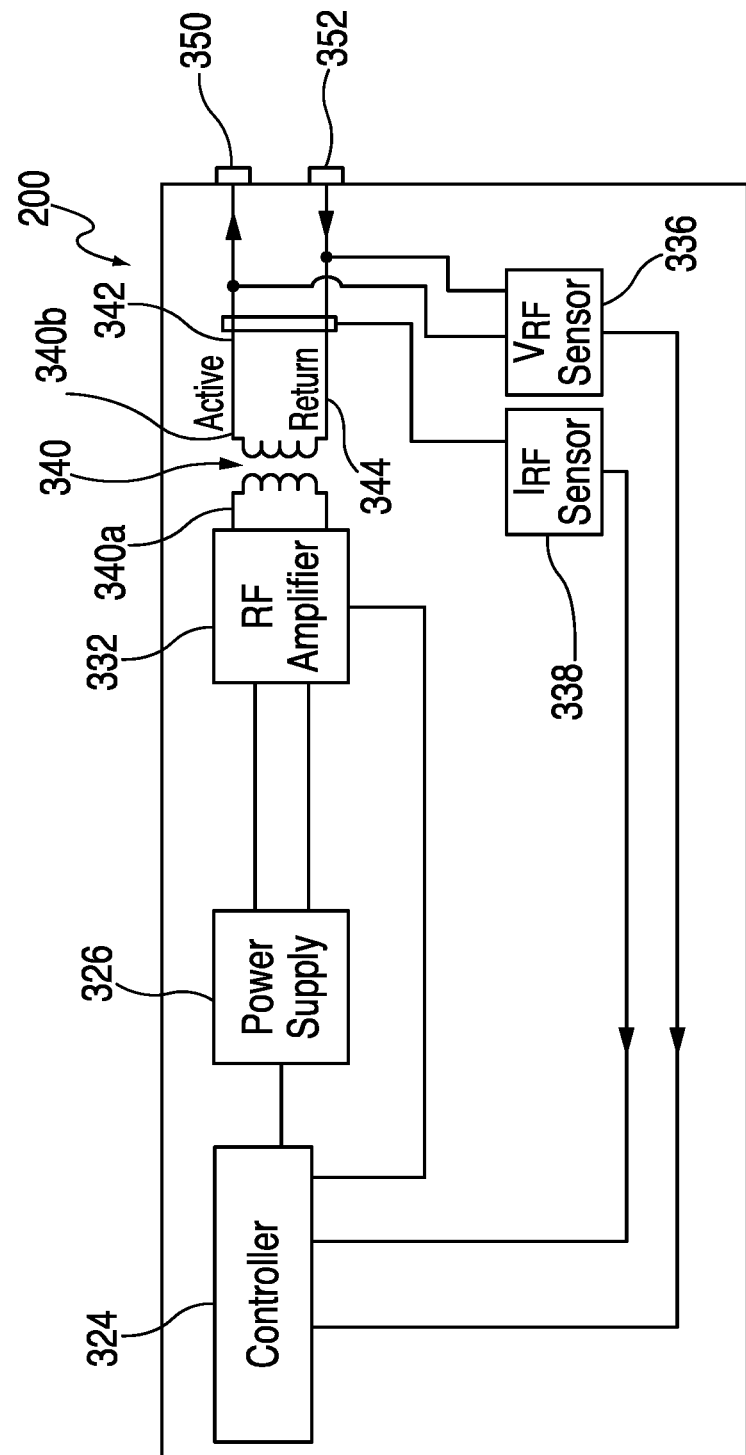
FIG. 3 is a schematic diagram of the electrosurgical generator of FIG. 2.

The system 10 may also include one or more bipolar electrosurgical instruments, for example, a bipolar electrosurgical forceps 30 having one or more electrodes for treating tissue of a patient. The electrosurgical forceps 30 includes a housing 31 and opposing jaw members 33 and 35 disposed at a distal end of a shaft 32. The jaw members 33 and 35 have one or more active electrodes 34 and a return electrode 36 disposed therein, respectively. The active electrode 34 and the return electrode 36 are connected to the generator 200 through cable 38 that includes the supply and return lines 24, 28, which may be coupled to the active and return terminals 350, 352, respectively (FIG. 3). The electrosurgical forceps 30 is coupled to the generator 200 at a port having connections to the active and return terminals 350 and 352 (e.g., pins) via a plug (not shown) disposed at the end of the cable 38, wherein the plug includes contacts from the supply and return lines 24, 28 as described in more detail below.

Figure 2:
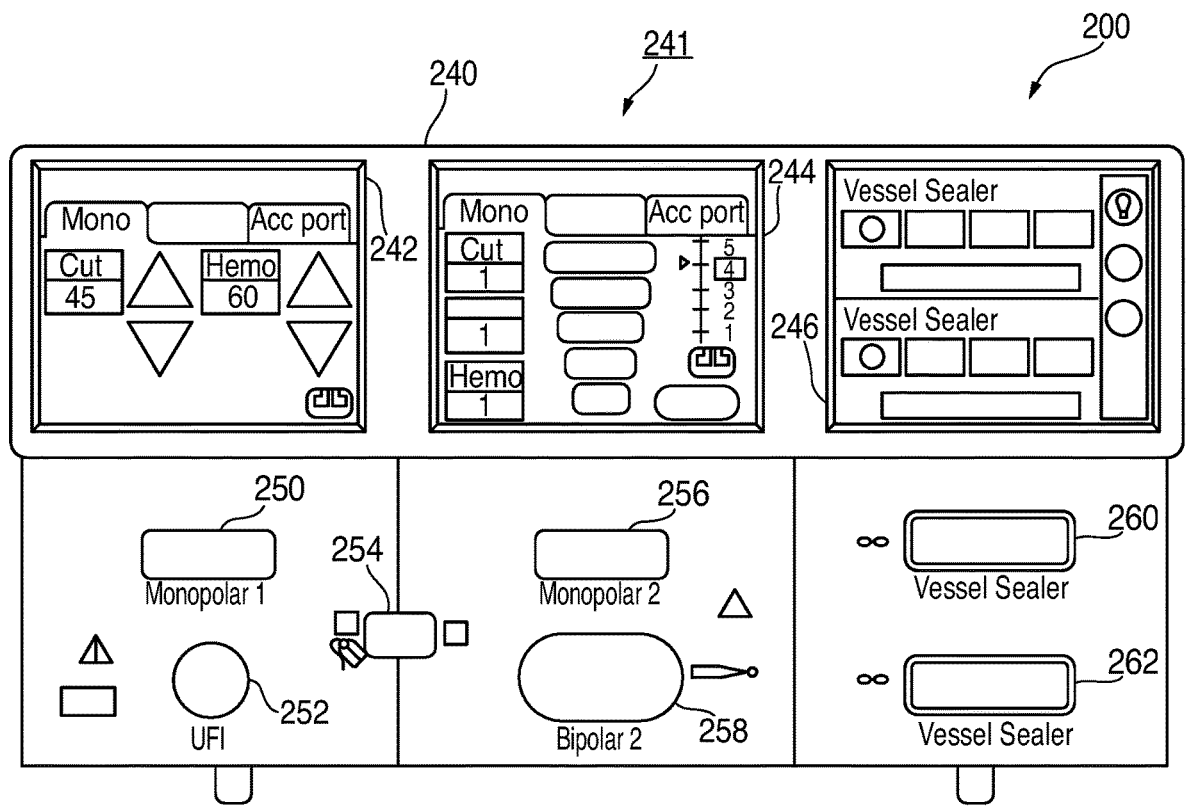
FIG. 2 is a front view of an electrosurgical generator of the electrosurgical system of FIG. 1.

With reference to FIG. 2, a front face 240 of the generator 200 is shown. The generator 200 may include a plurality of ports 250-262 to accommodate various types of electrosurgical instruments (e.g., monopolar electrosurgical instrument 20, electrosurgical forceps 30, etc.).

The generator 200 includes a user interface 241 having one or more display screens 242, 244, 246 for providing the user with variety of output information (e.g., intensity settings, treatment complete indicators, etc.). Each of the screens 242, 244, 246 is associated with a corresponding port 250-262. The generator 200 includes suitable input controls (e.g., buttons, activators, switches, touch screen, etc.) for controlling the generator 200. The screens 242, 244, 246 are also configured as touch screens that display a corresponding menu for the instruments (e.g., electrosurgical forceps 30, etc.). The user can adjust inputs by simply touching corresponding menu options.

Screen 242 controls monopolar output and the devices connected to the ports 250 and 252. Port 250 is configured to couple to a monopolar electrosurgical instrument (e.g., electrosurgical instrument 20) and port 252 is configured to couple to a foot switch (not shown). The foot switch provides for additional inputs (e.g., replicating inputs of the generator 200). The port 254 is configured to couple to the return electrode pad 26. Screen 244 controls monopolar and bipolar output and the devices connected to the ports 256 and 258. Port 256 is configured to couple to other monopolar instruments. Port 258 is configured to couple to a bipolar instrument (e.g., electrosurgical forceps 30).

Screen 246 controls the electrosurgical forceps 30 that may be plugged into one of the ports 260 and 262, respectively. The generator 200 outputs energy through the ports 260 and 262 suitable for sealing tissue grasped by the electrosurgical forceps 30. In particular, screen 246 outputs a user interface that allows the user to input a user-defined intensity setting for each of the ports 260 and 262. The user-defined setting may be any setting that allows the user to adjust one or more energy delivery parameters, such as power, current, voltage, energy, etc. or sealing parameters, such as energy rate limiters, sealing duration, etc. The user-defined setting is transmitted to a controller 324 (FIG. 3) where the setting may be saved in a memory (not shown). In embodiments, the intensity setting may be a number scale, such as for example, from one to ten or one to five. In embodiments, the intensity setting may be associated with an output curve of the generator 200. The intensity settings may be specific for each electrosurgical forceps 30 being utilized, such that various instruments provide the user with a specific intensity scale corresponding to the electrosurgical forceps 30. The active and return terminals 350 and 352 (FIG. 3) may be coupled to any of the desired ports 250-262.

With reference to FIG. 3, the generator 200 also includes a controller 324, a power supply 326, and a power converter 332. The power supply 326 may be a high voltage, DC power supply connected to an AC source (e.g., line voltage) and provides high voltage, DC power to the power converter 332, which then converts high voltage, DC power into RF energy and delivers the energy to the active terminal 350. (FIG. 2) The energy is returned thereto via the return terminal 352. In particular, electrosurgical energy for energizing the monopolar electrosurgical instrument 20 and/or electrosurgical forceps 30 is delivered through the active and return terminals 350 and 352. The active and return terminals 350 and 352 are coupled to the power converter 332 through an isolation transformer 340. More specifically, the isolation transformer 340 includes a primary winding 340*a* coupled to the power converter 332 and a secondary winding 340*b* having an active lead 342 coupled to the active terminal 350 and a return lead 344 coupled to the return terminal 352. The output of power converter 332 transmits current through the isolation transformer 340 to the load "Z", e.g., tissue being treated.

The power converter 332 is configured to operate in a plurality of modes, during which the generator 200 outputs corresponding waveforms having specific duty cycles, peak voltages, crest factors, etc. It is envisioned that in other embodiments, the generator 200 may be based on other types of suitable power supply topologies. Power converter 332 may be a resonant RF amplifier or a non-resonant RF amplifier. A non-resonant RF amplifier, as used herein, denotes an amplifier lacking any tuning components, e.g., inductors, capacitors, etc., disposed between the power converter and the load "Z" intended to establish a fixed operating frequency.

The controller 324 includes a processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to perform the calculations and/or set of instructions described herein.

The controller 324 includes output ports that are operably connected to the power supply 326 and/or the power converter 332 allowing the controller 324 to control the output of the generator 200 according to either open and/or closed control loop schemes. A closed loop control scheme is a feedback control loop, in which a plurality of sensors measure a variety of tissue and energy properties (e.g., tissue impedance, tissue temperature, output power, current and/or voltage, etc.), and provide feedback to the controller 324. The controller 324 then controls the power supply 326 and/or the power converter 332, which adjusts power delivered to and/or from the power converter 332, respectively. The controller 324 also receives input signals from the input controls of the generator 200, the electrosurgical instrument 20 and/or electrosurgical forceps 30. The controller 324 utilizes the input signals to adjust power outputted by the generator 200 and/or performs other control functions thereon.

The controller 324 may perform various mathematical computations in order to control the power supply 326 and/or the power converter 332 to generate an RF waveform having a desired shape and energy content. Examples of computations performed by the controller 324 include, but are not limited to, calculating instantaneous and/or root mean square power levels, amount of energy delivered on a cycle by cycle basis, load impedance, etc.

The generator 200 according to the present disclosure may also include a plurality of sensors, namely, a voltage sensor 336 and a current sensor 338. The voltage sensor 336 is coupled to the active and return leads 342, 344 and measure RF voltage supplied to the active and return terminals 350, 352. The current sensor 338 is coupled to the active and/or return leads 342, 344 and measures RF current supplied to the active and return terminals 350, 352. In embodiments, the generator 200 may also include additional sensors (not shown) coupled to the power supply 326.

Figure 4:
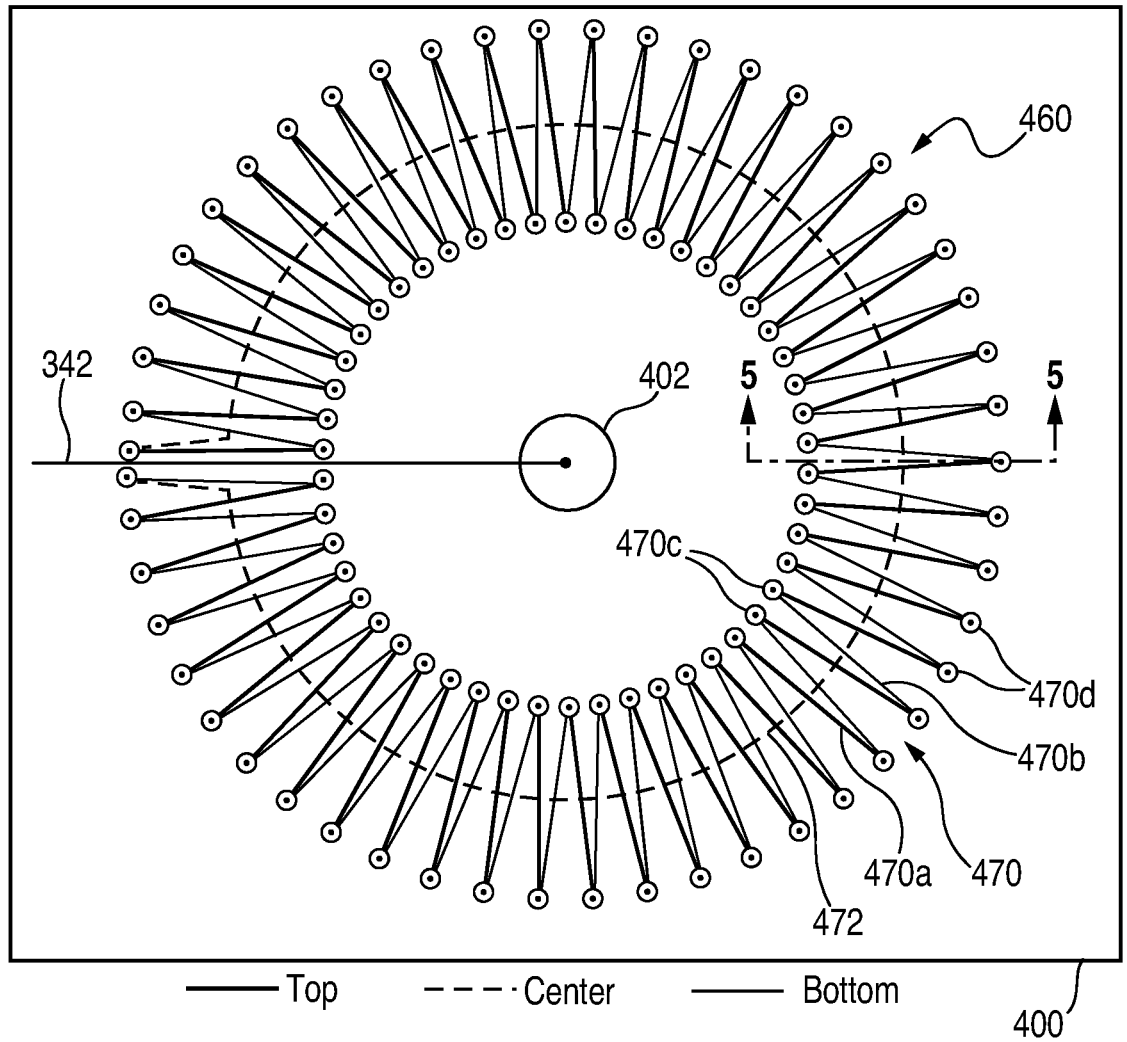
FIG. 4 is a schematic diagram of a planar magnetic device disposed on a printed circuit board.
Figure 5:
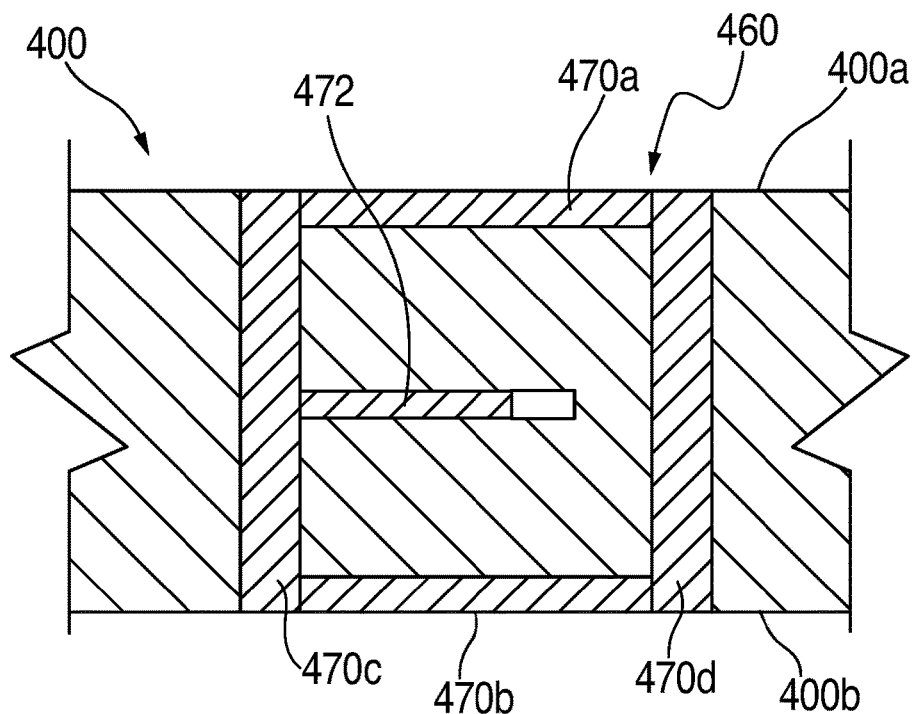
FIG. 5 is a cross-sectional side view taken along a sectional line 5-5 of the planar magnetic device of FIG. 4 according to an embodiment of the present disclosure.

With reference to FIGS. 4 and 5, the current sensor 338 includes a planar magnetic device 460, e.g., a current sense coil, which is disposed on a printed circuit board ("PCB") 400. The PCB 400 may be a multilayer PCB formed from any suitable dielectric material, including, but not limited to composite materials composed of woven fiberglass cloth with an epoxy resin binder such as FR-4 grade as designated by the National Electrical Manufacturers Association. The PCB 400 defines an opening 402 therethrough for passage of the active lead 342. The planar magnetic device 460 includes an outer coil 470 and an inner conductor 472. The outer coil 470 is formed by a plurality of upper and lower conductive traces 470*a* and 470*b* interconnected by a plurality of inner conductive vias 470*c* and outer conductive vias 470*d*. The upper and lower conductive traces 470*a* and 470*b* may be printed on respective upper and lower surfaces 400*a*, 400*b* (FIG. 5) of the PCB 400. The inner conductor 472 is disposed in between the upper and lower conductive traces 470*a* and 470*b* and is embedded within the PCB 400 (FIG. 5).

Figure 6:
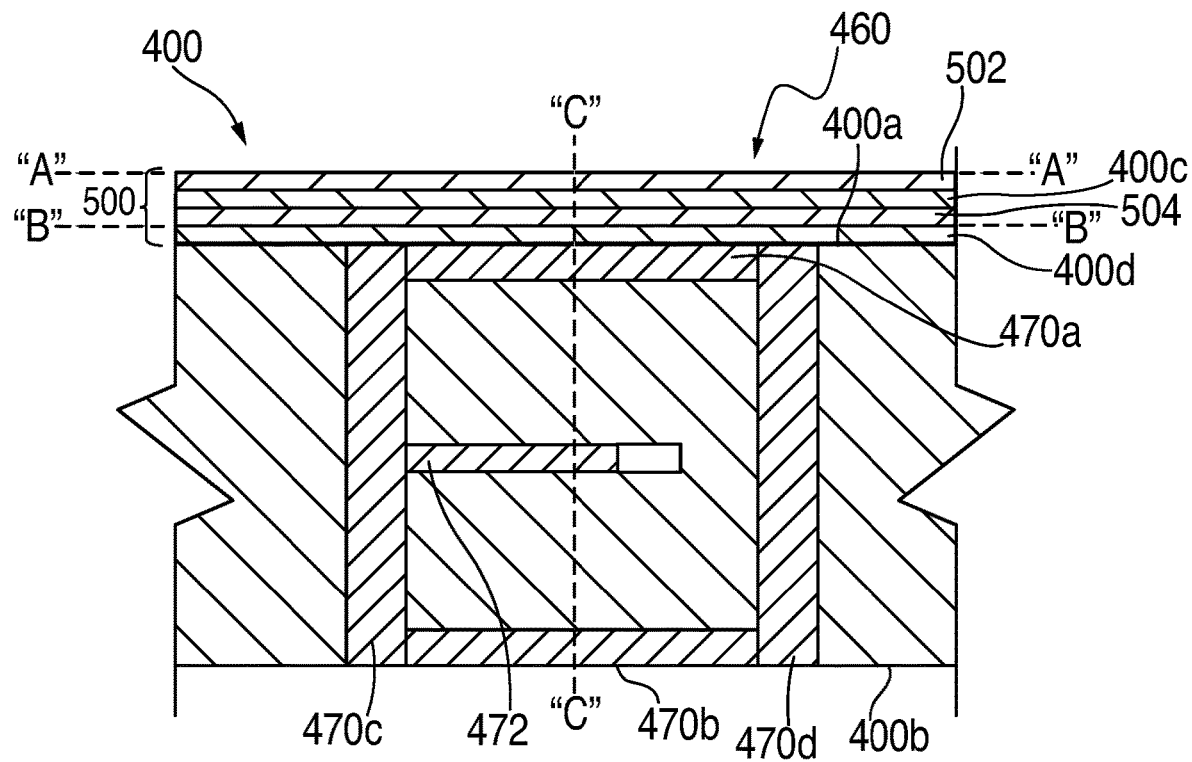
FIG. 6 is a cross-sectional side view of a planar magnetic device having an overlapping shield assembly according to another embodiment of the present disclosure.

FIG. 6 shows an overlapping shield assembly 500 disposed over the upper surface 400*a* of the PCB 400. The overlapping shield assembly 500 includes a first layer 502 and a second layer 504, which are separated by one or more dielectric layers 400*c*, 400*d*, . . . 400*n* of the PCB 400. In embodiments, the overlapping shield assembly 500 may also be disposed on the bottom surface 400*b* of the PCB 400. In other embodiments, the overlapping shield assembly 500 may be disposed internally, i.e., within the planar magnetic device 460, namely, between the upper conductive traces 470*a* and lower conductive traces 470*b*. This configuration provides significant internal device E-field shielding and isolation and is suitable to control crosstalk and leakage currents. In further embodiments, the first layer 502 may be disposed on the upper surface 400*a* of the PCB 400 and the second layer 504 may be disposed on the lower surface 400*b* of the PCB 400. A single layer of shielding (e.g., the first layer 502 or the second layer 504) may be on each surface 400*a*, 400*b* of the PCB 400 and may provide sufficient E-field shielding and may be adequate for many applications. In additional embodiments, a pair of overlapping shield assemblies 500 may be disposed on the PCB 400, one on each surface 400a, 400b, respectively, to provide an additional order of magnitude of shielding.

Figure 7:
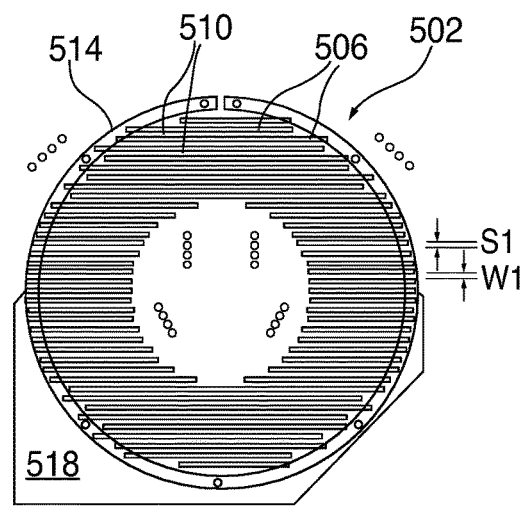
FIG. 7 is a plan view of a first layer of the overlapping shield assembly of FIG. 6.
Figure 8:
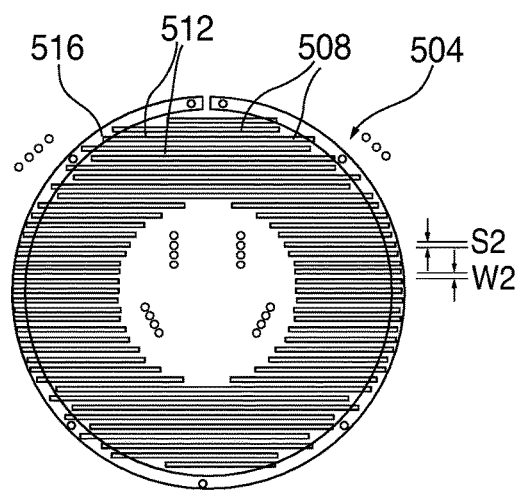
FIG. 8 is a plan view of a second layer of the overlapping shield assembly of FIG. 6.
Figure 9:
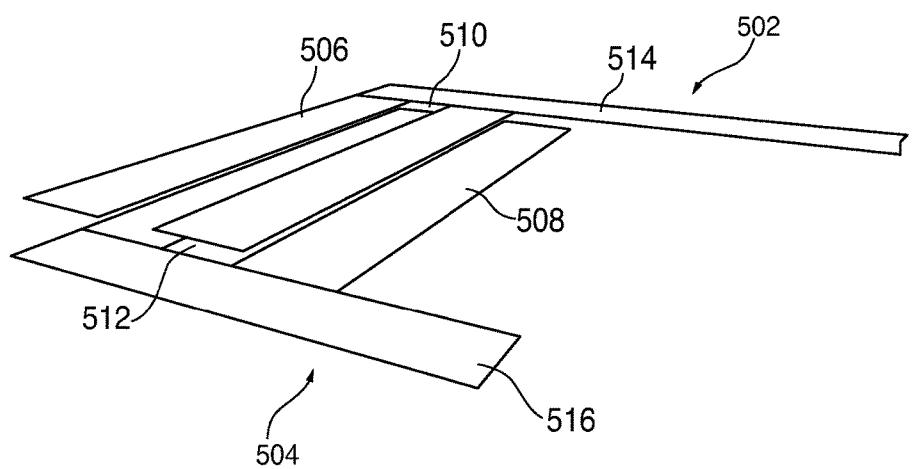
FIG. 9 is a perspective view of the overlapping shield assembly of FIG. 6.

With reference to FIGS. 6-9, the first and second layers 502 and 504 may be formed as conductive traces on their corresponding dielectric layers 400c and 400d (FIG. 6) of the PCB 400. Thus, the first layer 502 is disposed in a first plane "A-A" and the second layer 504 is disposed in a second plane "B-B" (FIG. 6). Each of the layers 502 and 504 includes a plurality of strips 506 and 508, respectively. The strips 506 and 508 are arranged in parallel with periodic gaps 510 and 512 that are defined therebetween. As shown in FIG. 7, the strips 506 of the first layer 502 have a strip width s1 and the gaps 510 have a gap width w1. Similarly, the strips 508 of the second layer 504 have a strip width s2 and the gaps 512 have a gap width w2. The strip width s1 of the strips 506 is substantially equal to the gap width w2 of the gaps 512 of the second layer 504 and conversely, strip width s2 of the strips 508 is substantially equal to the gap width w1 of the gaps 510 of the first layer 502. This configuration allows for the strips 506, 508 and the gaps of 510, 512 to overlap, respectively, thus forming an EMI shield.

Strip widths s1 or s2 may be from about 0.1 millimeters (mm) to about 10 mm, in embodiments from about 1 mm to about 5 mm. Since gap widths w1 and w2 are related to the strip widths s1 and s2, gap widths w1 and w2 may also have the same dimensions. In further embodiments, the strip width s1 or s2 of each of the strips 506 and 508 may be different, i.e., have a non-uniform width.

Each of the first layer 502 and the second layer 504 also includes a perimeter conductor 514 and 516, respectively. The perimeter conductor 514 is coupled to each of the strips 506 of the first layer and the perimeter conductor 516 is coupled to each of the strips 508 of the second layer 504. In addition, the first and second layers 502 and 504 are interconnected by one or more conductors 518 to form the EMI shield.

Because the strips 506 and 508 are spaced apart, i.e., do not form a continuous conductive surface across one plane "A-A" or "B-B," respectively, and are open ended, they do not form a complete circuit for stray current to flow therethrough. Furthermore, because the strips 506 and 508 are relatively narrow, Eddy currents, also known as Foucalt currents, do not have a significant impact. However, because the first and second layers 502 and 504 are separated by one or more PCB layers of the PCB 400, the height between the layers is comparatively small, thereby forming a continuous surface when viewed along an axis "C-C," which is transverse with respect to each of the planes "A-A" and "B-B" (FIG. 6). Put differently, the first and second layers 502 and 504 complement each other to form, i.e., complete, the overlapping shield assembly 500.

While several embodiments of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope of the claims appended hereto.

What is claimed is:

1. An electrosurgical generator comprising:
a power supply configured to output a direct current;
a power converter coupled to the power supply, the power converter configured to convert the direct current into a radio frequency current;
at least one lead coupling the power converter to a terminal configured to couple to an electrosurgical instrument; and
a current sensor configured to sense the radio frequency current, the current sensor including:
a multilayered dielectric substrate including a plurality of dielectric layers;
at least one component of the current sensor disposed on at least one internal dielectric layer of the plurality of dielectric layers; and
an overlapping shield assembly including a first shield layer and a second shield layer separated by at least one of the plurality of dielectric layers, the first shield layer having a plurality of first strips separated by a first plurality of gaps and the second shield layer having a plurality of second strips separated by a second plurality of gaps, the plurality of first strips and the plurality of second strips are parallel relative to each other with the first plurality of strips overlapping the second plurality of gaps and the second plurality of strips overlapping the first plurality of gaps.

2. The electrosurgical generator according to claim 1, wherein each of the plurality of first strips has a first width and the plurality of first strips are separated by a first gap width.

3. The electrosurgical generator according to claim 2, wherein each of the plurality of second strips has a second width and the plurality of second strips are separated by a second gap width.

4. The electrosurgical generator according to claim 3, wherein the first width is substantially equal to the second gap width and the second width is substantially equal to the first gap width.

5. The electrosurgical generator according to claim 2, wherein the first shield layer includes a first perimeter conductor coupled to each of the plurality of first strips and the second shield layer includes a second perimeter conductor coupled to each of the plurality of second strips.

6. The electrosurgical generator according to claim 5, wherein the first shield layer is electrically coupled to the second shield layer.

7. The electrosurgical generator according to claim 1, wherein the current sensor includes:
a first outer coil configured to detect a first magnetic field generated by the radio frequency current;
a second outer coil configured to detect the first magnetic field, the second outer coil further configured to cancel an electrical field induced in the first outer coil; and
an inner conductor disposed between the first outer coil and the second outer coil, the inner conductor configured to detect a second magnetic field generated by the radio frequency current.

8. The electrosurgical generator according to claim 7, wherein each of the first outer coil, the second outer coil, and the inner conductor is disposed on a corresponding internal dielectric layer of the plurality of dielectric layers.

* * * * *